United States Patent [19]

Ehrenfreund

[11] 4,431,671

[45] * Feb. 14, 1984

[54] PHENYLUREAS

[75] Inventor: Josef Ehrenfreund, Manchester, England

[73] Assignee: Ciba-Geigy Corporation, Ardsley, N.Y.

[*] Notice: The portion of the term of this patent subsequent to Apr. 6, 1999 has been disclaimed.

[21] Appl. No.: 326,998

[22] Filed: Dec. 3, 1981

[30] Foreign Application Priority Data

Dec. 12, 1980 [CH] Switzerland .......................... 9197/80
Oct. 29, 1981 [CH] Switzerland .......................... 6915/81

[51] Int. Cl.³ ..................... A01N 47/34; C07C 127/22
[52] U.S. Cl. ..................................... 424/322; 564/44; 564/305; 564/442
[58] Field of Search ................ 424/322; 564/44, 305, 564/442

[56] References Cited

U.S. PATENT DOCUMENTS 3,121,116  2/1964  Pawloski ............................. 564/305
3,475,156 10/1969  Olin ................................. 564/305 X
4,139,636  2/1979  Sirrenberg et al. ............... 564/44 X
4,162,330  7/1979  Ehrenfreund ..................... 564/44 X
4,310,694  1/1982  Ehrenfreund ..................... 564/44 X
4,323,579  4/1982  Ehrenfreund ..................... 564/44 X Primary Examiner—Robert V. Hines
Attorney, Agent, or Firm—Frederick H. Rabin; Bruce M. Collins

[57] ABSTRACT

Substituted N-(p-aminophenyl)-N'-benzoylureas of the formula

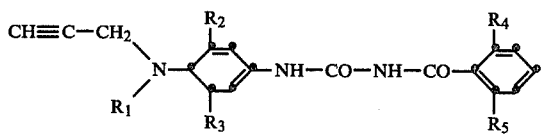

wherein $R_1$ is hydrogen, $C_1$–$C_4$-alkyl or propargyl; $R_2$ and $R_3$ are each hydrogen or halogen; $R_4$ is methyl or halogen; and $R_5$ is hydrogen or halogen. Processes for producing these compounds and their use for combating pests, particularly their use as insecticides, are described.

16 Claims, No Drawings

PHENYLUREAS

The present invention relates to novel substituted N-(p-aminophenyl)-N'-benzoylureas, to processes for producing them, and to their use for combating pests.

The substituted N-(p-aminophenyl)-N'-benzoylureas according to the invention have the formula

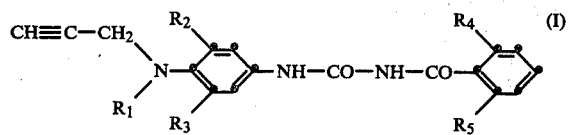

wherein $R_1$ is hydrogen, $C_1$-$C_4$-alkyl or propargyl, $R_2$ and $R_3$ are each hydrogen or halogen, $R_4$ is methyl or halogen, and $R_5$ is hydrogen or halogen.

Examples of alkyl groups in the definition of $C_1$-$C_4$-alkyl according to the invention are methyl, ethyl, n-propyl and i-propyl, as well as the four isomeric butyl groups. And by halogen within the scope of the invention is meant fluorine, chlorine, bromine or iodine, preferably fluorine, chlorine or bromine.

Compounds of the formula I preferred on account of their action as pesticidal active substances are those wherein $R_1$ is $C_1$-$C_4$-alkyl or propargyl; $R_2$ and $R_3$ are each fluorine, chlorine or bromine; $R_4$ is fluorine, chlorine, bromine or methyl; and $R_5$ is hydrogen, fluorine or chlorine. Of most interest within this group are those compounds wherein $R_1$, $R_2$, $R_3$ and $R_5$ have the given meanings, and $R_4$ is fluorine or chlorine, and alternatively those compounds in which $R_1$, $R_2$, $R_3$ and $R_4$ have the given meanings, and $R_5$ is fluorine or chlorine.

To be emphasised also are those compounds of the formula I wherein $R_1$ is $C_1$-$C_4$-alkyl or propargyl, $R_2$ and $R_3$ are each fluorine, chlorine or bromine, $R_4$ is fluorine or chlorine, and $R_5$ is hydrogen or fluorine. Most preferred in this group are on the one hand those compounds in which $R_1$, $R_2$ and $R_3$ have the given meanings, and $R_4$ and $R_5$ are each fluorine, and on the other hand those compounds in which $R_1$, $R_2$, $R_3$ and $R_4$ have the given meanings, and $R_5$ is hydrogen.

The compounds of the formula I can be produced by processes known per se (cp., inter alia, the German Offenlegungsschriften Nos. 2,123,236 and 2,601,780). Thus, for example, a compound of the formula I can be obtained by reaction (a) of a compound of the formula II

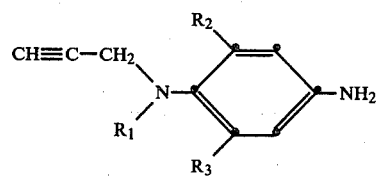

with a compound of the formula III

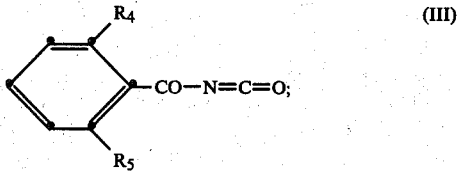

(b) of a compound of the formula IV

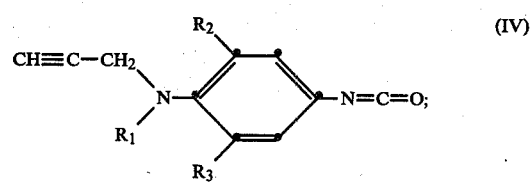

with a compound of the formula V

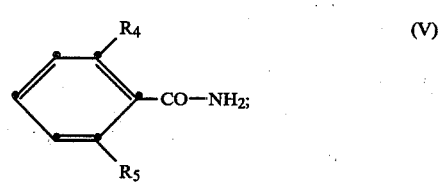

or (c) of a compound of the formula II with a compound of the formula VI

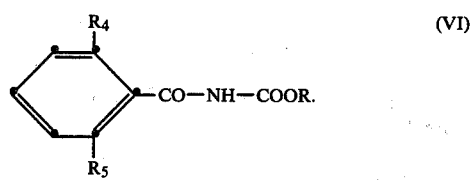

In the compounds of the formulae II, III, IV, V and VI, the symbols $R_1$ to $R_5$ have the meanings defined under the formula I, and R is a $C_1$-$C_8$-alkyl group, which is unsubstituted or substituted by halogen.

The processes (a), (b) and (c) mentioned are preferably performed under normal pressure and in the presence of an organic solvent or diluent. Suitable solvents or diluents are for example: ethers and etheral compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chloride, carbon tetrachloride and chlorobenzene; nitriles, such as acetonitrile or propionitrile; dimethyl sulfoxide, as well as ketones, for example acetone, methyl ethyl ketone, methyl-isopropyl ketone and methylisobutyl ketone. Process (a) is in general performed at a temperature of $-10°$ to $100°$ C., preferably between $15°$ and $25°$ C., optionally in the presence of an organic base, for example triethylamine. Process (b) is carried out at a temperature of $0°$ to $150°$ C., preferably at the boiling point of the solvent used, and optionally in the presence of an organic base, such as pyridine, and/or with the addition of an alkali metal or alkaline-earth metal, preferably sodium. For the reaction (c), that is to say, for the reaction of the urethanes of the formula VI with a compound of the formula II, temperatures of between about 60° C. and the boiling point of the respective reaction mixture are preferred, the employed solvents being in particular aromatic hydrocarbons, such as toluene, xylene, chlorobenzene, and so forth.

The starting materials of the formulae III, V and VI in the foregoing are known, or in cases where they are new they can be produced by processes analogous to known processes.

The compounds of the formula II are novel and, as starting compounds leading to the valuable pesticidal active substances of the formula I, likewise form subject matter of the present invention. They can be produced for example by chemical reduction of corresponding substituted nitrobenzenes of the formula VII

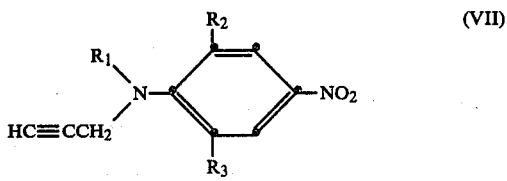

by means of iron in aqueous acids. The substituted nitrobenzenes of the formula VII are for their part produced by N-propargylation of corresponding nitro compounds of the formula VIII

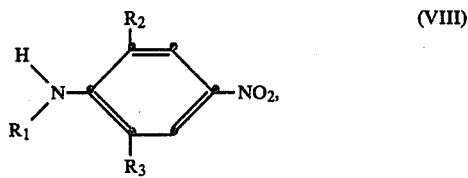

in a manner for example analogous to that described in the U.S. Pat. No. 3,121,745. The isocyanates of the formula IV are obtainable for example by reacting the corresponding N,N-substituted p-phenylenediamines of the formula II with phosgene, using in general customary processes. The benzamides of the formula V and the benzoylisocyanates of the formula III can be obtained as follows (cp. J. Agr. Food Chem. 21(3), 348 and 993; 1973):

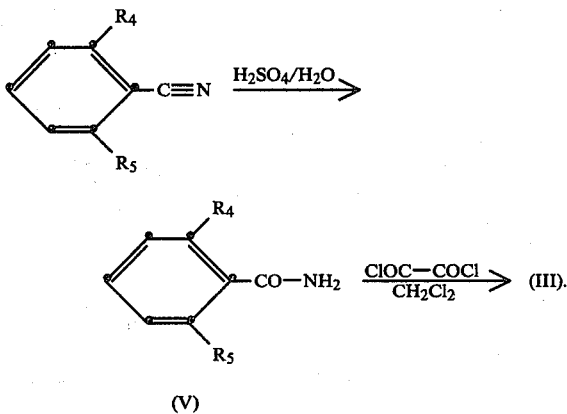

The aforementioned benzamides of the formula V to be used as starting materials are for the most part known (cp. Beilstein "Handbuch der organischen Chemie" Vol. 9, p. 336). The urethanes of the formula VI can be obtained, in a manner known per se, by reaction of a benzoylisocyanate of the formula III with a corresponding alcohol, or by reaction of a benzamide of the formula V, in the presence of a basic compound, with a corresponding ester of chloroformic acid.

It is already known that certain N-phenyl-N'-benzoylureas have insecticidal properties (cp. German Offenlegungsschriften Nos. 2,123,236, 2,504,982, 2,537,413, 2,601,780 and 2,726,684, the Belgian Patent Specifications Nos. 832,304, 743,906, 844,066 and 867,046, and also the U.S. Pat. No. 4,089,975). The German Offenlegungsschrift No. 2,926,480 relates to substituted N-(p-alkylenephenylamino)-phenyl-N'-benzoylureas and -thioureas having insecticidal activity. From J. Arg. Food Chem. 21, No. 3, 348 ff. (1973) are also known substituted N-phenyl-N'-2,6-dichlorobenzoylureas, which are said to have insecticidal properties. There are mentioned on page 353 of this publication corresponding N-(4-dimethylamino)-phenyl derivatives and N-(3-chloro-4-dimethylamino)-phenyl derivatives, which however—as can be seen from the Table III given therein—have an inadequate insecticidal action. The European Patent Application No. 16729 describes substituted N-(p-alkenylamino)-phenyl-N'-benzoylureas which likewise have insecticidal properties.

It has now been found that, surprisingly, the compounds of the formula I according to the invention, whilst having high tolerance to plants and negligible toxicity to warmblooded animals, exhibit a degree of effectiveness as pesticidal active substances which is greater than that exhibited by the aforementioned compounds known from the prior art.

The compounds of the formula I are particularly suitable for combating insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera.

Besides having a very favourable action against flies, for example Musca domestica, and against mosquito larvae, the compounds of the formula I are suitable also for combating insects that damage plants by eating, in crops of ornamental plants and productive plants, especially in cotton crops (for example against *Spodoptera littoralis* and *Heliothis virescens*), and also in fruit and vegetable crops (for example against *Leptinotarsa decemlineata, Pieris brassicae* and *Laspeyresia pomonella*). To be emphasised in particular is the ovicidal and ovolarvicidal action of the compounds of the formula I. When compounds of the formula I are taken up with the feed by adult insects, there is observed in many cases, especially with Coleoptera, for example *Anthonomus grandis*, a reduced oviposition and/or a lessened rate of hatching.

The compounds of the formula I are moreover suitable for combating ectoparasites in both domestic and productive animals, for example by treatment of animals, livestock housing and pasture land.

The good insecticidal action of the compounds of the formula I according to the invention corresponds to a mortality rate of at least 50–60% of the harmful insects mentioned.

The action of the compounds according to the invention can be considerably broadened and adapted to suit given circumstances by the addition of other insecticides and/or acaricides. Suitable additives are for example the following active substances: organic phosphorus compounds, nitrophenols and derivatives thereof, formamidines, ureas, pyrethroids, carbamates, chlorinated hydrocarbons and Bacillus thuringiensis preparations.

The compounds of the formula I can be combined with particular advantage also with substances which intensify pesticidal activity. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used. These forms of preparation are particularly suitable for combating zooparasitic pests.

The compounds of the formula I are used either in an unmodified form or preferably together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I, or combinations of this active ingredient with other insecticides or acaricides, and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalates, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. A great number of pre-granulated materials of inorganic or organic nature, such as in particular dolomite or ground plant residues, can also be used.

Suitable surface-active compounds are, depending on the nature of the active substance of the formula I, or of the combinations of this active substance with other insecticides or acaricides, to be formulated, nonionic, cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$–$C_{22}$), for example the sodium or potassium salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and they generally contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethyl ammonium chloride or benzyldi-(2-chloroethyl)-ethylammonium bromide.

The tensides customarily used in formulation practice are described, inter alia, in the following publications: "Mc Cutcheon's Detergents and Emulsifiers Annual", MC Publishing Corp., Ringwood, N.J., 1979, and Sisely and Wood, "Encyclopedia of Surface Active Agents", Chemical Publishing Co., Inc. New York.

The pesticidal preparations contain as a rule 0.1 to 99%, particularly 0.1 to 95%, of active substance of the formula I, or of combinations of this active substance with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule preparations having considerably lower concentrations of active substance.

The compositions can also contain additives such as stabilisers, antifoam agents, viscosity regulators, binders and adhesives, as well as fertilisers or other active substances for obtaining special effects.

Formulation examples for liquid active substances of the formula I or combinations of these active substances with other insecticides or acaricides (%=percent by weight)

| 1. Emulsion concentrates | (a) | (b) | (c) |
|---|---|---|---|
| active substance or active substance combination | 20% | 40% | 50% |
| calcium dodecylbenzenesulfonate | 5% | 8% | 5.8% |
| castor-oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| 2. Solutions | (a) | (b) | (c) | (d) |
|---|---|---|---|---|
| active substance or active-substance combination | 80% | 10% | 5% | 95% |
| ethylene glycol-monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active substance or active-substance combination | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 4. Dusts | (a) | (b) |
|---|---|---|
| active substance or active-substance combination | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

Formulation examples for solid active substances of the formula I or combinations of these active substances with other insecticides or acaricides (%=percent by weight)

| 5. Wettable powders | (a) | (b) |
|---|---|---|
| active substance or active-substance combination | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active substance or the active substance combination is well mixed with the additives, and the mixture is thoroughly ground in a suitable mill. Wettable powders which can be diluted with water to give suspensions of the required concentration are obtained.

| 6. Emulsion concentrate | |
|---|---|
| active substance or active-substance combination | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the required concentration can be obtained from this concentration by dilution with water.

| 7. Dusts | (a) | (b) |
|---|---|---|
| active substance or active-substance combination | 5% | 8% |
| talcum | 95% | — |
| kaolin | — | 92% |

Dusts ready for use are obtained by mixing the active substance with the carrier and grinding the mixture in a suitable mill.

| 8. Extruder granulate | |
|---|---|
| active substance or active-substance combination | 10% |
| sodium lignin sulfonate | 2% |
| carboxymethylcellulose | 1% |
| kaolin | 87% |

The active substance is mixed and ground with the additives, and the mixture is moistened with water. This mixture is extruded, granulated, and subsequently dried in a stream of air.

| 9. Coated granules | |
|---|---|
| active substance or active-substance combination | 3% |
| polyethylene glycol (MG 200) | 3% |
| kaolin | 94% |

The finely ground active substance or the active-substance combination is evenly applied, in a mixer, to the kaolin moistened with polyethylene glycol. Dustfree coated granules are obtained in this manner.

| 10. Suspension concentrate | |
|---|---|
| active substance or active-substance combination | 40% |
| ethylene glycol | 10% |
| nonylphenol-polyethylene glycol (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active substance or the active-substance combination is intimately mixed with the additives. There is thus obtained a suspension concentrate from which can be prepared, by dilution with water, suspensions of the concentration required.

EXAMPLE 1

(a) Production of 3,5-dichloro-4-(N-methyl-N-propargyl)-aminoaniline 33.15 g of 3,5-dichloro-4-N-methyl-amino-nitrobenzene, 20 g of powdered NaOH, 24 g of propargyl bromide and 3.8 g of tetrabutylammonium hydrogen sulfate in 250 ml of toluene are stirred at 20° C. for 15 hours, and subsequently heated at 60° C. for 4 hours. The mixture is filtered after cooling and the filtrate, after removal of the solvent, is chromatographed through silica gel with hexane/diethyl ether (10:1) as the eluant. Recrystallisation from hexane yields the compound of the formula

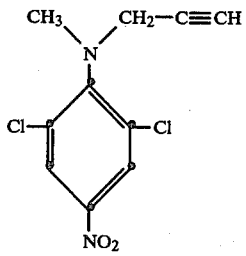

having a melting point of 54°–56° C.

13.4 g of 3,5-dichloro-4-(N-methyl-N-propargyl)-aminonitrobenzene are placed into 50 ml of tetrahydrofuran and 200 ml of 5% acetic acid, and at reflux temperature are added portionwise 45 g of iron powder. After the addition is completed, the mixture is cooled, filtered, and the filtrate is extracted three times with diethyl ether. The solvent is removed and the crude product is chromatographed through silica gel with hexane/diethyl ether (10:1) as the eluant. There is thus obtained the compound of the formula

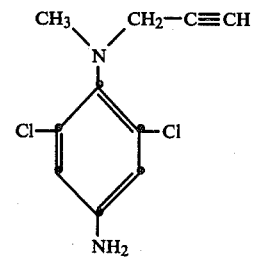

as a yellowish oil.

(b) Production of N-[3,5-dichloro-4-(N-methyl-N-propargyl)amino]-phenyl-N'-2-chlorobenzoylurea 3.7 g of 3,5-dichloro-4-(N-methyl-N-propargyl)-aminoaniline are dissolved in a small amount of anhydrous ether, and, with cooling and the exclusion of moisture, 2.9 g of 2-chlorobenzoylisocyanate are added. The precipitate is filtered off with suction, and recrystallised from alcohol to thus obtain the compound of the formula

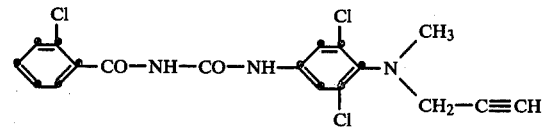

having a melting point of 138°–140° C. (compound No. 1).

The following compounds of the formula I are produced by a procedure analogous to that described in the foregoing:

| Comp. No. | $R_1$ | $R_2$ | $R_3$ | $R_4$ | $R_5$ | Melting point (°C.) |
|---|---|---|---|---|---|---|
| 2 | —CH₃ | Cl | Cl | Cl | H | 138–140 |
| 3 | —CH₃ | Cl | Cl | F | H | 156,5–159 |
| 4 | —CH₃ | Cl | Cl | Cl | F | 168–169 |
| 5 | —C₂H₅ | Cl | Cl | F | F | 133–134 |
| 6 | —CH₂≡CH | Cl | Cl | F | F | 155–156 |
| 7 | —CH₃ | Cl | Br | F | F | 179–180,5 |
| 8 | —CH₃ | Cl | Br | Cl | H | 120–122 |
| 9 | —CH₃ | Cl | Br | F | H | 162–164,5 |
| 10 | —C₂H₅ | Cl | Cl | F | H | 127–128 |
| 11 | —C₂H₅ | Cl | Cl | Cl | H | 150–151 |
| 12 | —(CH₂)₃CH₃ | Cl | Cl | Cl | H | 159–161 |
| 13 | —(CH₂)₃CH₃ | Cl | Cl | F | H | 74–76 |
| 14 | —(CH₂)₂CH₃ | Cl | Cl | F | F | 176–179 |
| 15 | —(CH₂)₂CH₃ | Cl | Cl | Cl | F | 178–180 |
| 16 | —(CH₂)₂CH₃ | Cl | Cl | Cl | H | 134–136 |
| 17 | —(CH₂)₂CH₃ | Cl | Br | F | H | 90–92 |
| 18 | —(CH₂)₂CH₃ | Cl | Br | Cl | H | 168–170 |
| 19 | —(CH₂)₂CH₃ | Cl | Br | F | F | 178–181 |

Also the following compounds of the formula I are obtainable by the procedure described in the foregoing:

| Comp. No. | $R_1$ | $R_2$ | $R_3$ | $R_4$ | $R_5$ |
|---|---|---|---|---|---|
| 20 | —CH₃ | Cl | Cl | Br | H |
| 21 | —CH₃ | Cl | Cl | CH₃ | H |
| 22 | —CH₃ | F | Cl | F | F |

-continued

| Comp. No. | R₁ | R₂ | R₃ | R₄ | R₅ |
|---|---|---|---|---|---|
| 23 | —CH₃ | F | Cl | Cl | H |
| 24 | —CH₃ | Br | F | Cl | H |
| 25 | —CH₃ | Br | F | F | F |
| 26 | —CH₃ | Cl | F | F | H |
| 27 | —(CH₂)₂CH₃ | Cl | Cl | F | H |
| 28 | —(CH₂)₃CH₃ | Cl | Cl | F | F |
| 29 | —CH₂—C≡CH | Cl | Cl | Cl | H |
| 30 | —CH₂—C≡CH | Cl | Cl | F | Cl |
| 31 | H | Cl | Cl | F | F |

EXAMPLE 2

Action against Lucilia sericata 1 ml of an aqueous solution containing 0.5% of active substance was added to 9 ml of a culture medium at 50° C. About 30 freshly hatched *Lucilia sericata* maggots were then placed onto the culture medium, and after 48 and 96 hours, respectively, the insecticidal action was determined by ascertaining the mortality rate.

Compounds according to Example 1 exhibit in this test a good action against Lucilia sericata.

EXAMPLE 3

Action against Aëdes aegypti

Sufficient of a 0.1% acetonic solution of the respective active substance was transferred by pipette to the surface of 150 ml of water in a container to obtain concentrations of 10, 5 and 1 ppm in each case. After the acetone had evaporated off, 30–40 three-day-old Aëdes larvae were placed into each container. The mortality rate was ascertained after 1, 2 and 5 days.

Compounds according to Example 1 exhibit in this test a good action against Aëdes aegypti.

EXAMPLE 4

Insecticidal stomach-poison action

Potted cotton plants about 25 cm in height were sprayed with aqueous active-substance emulsions containing the active substance in concentrations of 800, 400, 200, 100, 50, 12.4 and 3.0 ppm. After the drying of the applied coating, larvae of Spodoptera littoralis in the L₃-stage and of Heliothis virescens in the L₃-stage, respectively, were settled onto the cotton plants. The test was carried out at 24° C. with 60° C. relative humidity. The % mortality rate of the test insects was determined after 120 hours.

The following Table shows the results of biological tests on compounds according to the invention on the basis of the above biological Examples. The criterion applied for assessing the results of the tests was the % mortality rate, the scale of ratings used being as follows:
A: 80–100% mortality rate at a concentration of 3.0 ppm of the compound tested;
B: 80–100% mortality rate at a concentration of 12.5 ppm of the compound tested;
C: 80–100% mortality rate at a concentration of 50 ppm of the compound tested;
D: 80–100% mortality rate at a concentration of 100 ppm of the compound tested;
E: 80–100% mortality rate at a concentration of 200 ppm of the compound tested;
F: 80–100% mortality rate at a concentration of 400 ppm of the compound tested; and
G: less than 80% mortality rate at a concentration of 800 ppm of the compound tested.

| Compound No. | Pesticidal effectiveness Spodoptera larvae (Example 4) | Heliothis larvae (Example 4) |
|---|---|---|
| 1 | A | B |
| 2 | B | C |
| 3 | C | D |
| 4 | A | C |
| 5 | B | B |
| 6 | A | C |
| 7 | B | C |
| 8 | A | B |
| 9 | F | G |
| 10 | B | E |

EXAMPLE 5

Ovicidal action on *Spodoptera littoralis*

Eggs of *Spodoptera littoralis*, not older than 24 hours and deposited on filter paper, were cut out of the paper and immersed in a solution of 400 ppm of the active substance in an acetone/water mixture (1:1), the duration of immersion being one minute. The deposited eggs treated in this manner were then removed from the solution, and placed at 28° C. with 60% relative humidity into plastic dishes. An assessment was made after five days of the hatching rate, that is, of the number of larvae which had developed from the treated eggs.

Compounds according to Example 1 exhibit in the above test a good action.

EXAMPLE 6

Action on *Laspeyresia pomonella* (eggs)

Deposited *Laspeyresia pomonella* eggs, which were not older than 24 hours, were immersed on filter paper for 1 minutes in an acetonic-aqueous solution containing 12.5 ppm of the active substance to be tested. After the solution had been dried off, the eggs were transferred to Petri dishes and kept at a temperature of 28° C. The percentage rate of hatching from the treated eggs was determined after 6 days.

The compounds Nos. 4 and 5 according to Example 1 exhibited in the above test a 100% action. Other compounds according to Example 1 likewise proved very effective in this test.

EXAMPLE 7

Effect on reproduction of *Anthonomus grandis*

Adult *Anthonomus grandis*, which had been hatched no longer than 24 hours, were transferred, in groups each of 25 beetles, to cages having lattice walls. The cages containing the beetles were then immersed for 5 to 10 seconds in an acetonic solution containing 1.0 percent by weight of the active substance to be tested. After the beetles were again dry, they were placed, for copulation and oviposition, into covered dishes containing feed. Deposited eggs were flushed out with running water two to three times weekly; they were counted, disinfected by being placed for two to three hours in an aqueous disinfectant (such as "Actamer B 100"), and then deposited into dishes containing a suitable larval diet. An examination was made after 7 days to determine whether larvae had developed from the deposited eggs.

In order to ascertain the duration of the reproduction-influencing effect of the active substances tested, the oviposition of the beetles was observed during a period of about four weeks. The evaluation was on the basis of the reduction of the number of eggs laid and larvae hatched in comparison with that in the case of untreated control specimens.

Compounds according to Example 1 exhibit in the above test a good action with regard to reducing reproduction.

What is claimed is:

1. A compound of the formula I

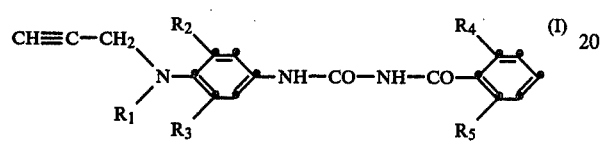

wherein $R_1$ is hydrogen, $C_1$-$C_4$-alkyl or propargyl; $R_2$ and $R_3$ are each hydrogen or halogen; $R_4$ is methyl or halogen; and $R_5$ is hydrogen or halogen.

2. A compound according to claim 1, wherein $R_1$ is $C_1$-$C_4$-alkyl or propargyl; $R_2$ and $R_3$ are each fluorine, chlorine or bromine; $R_4$ is fluorine, chlorine, bromine or methyl; and $R_5$ is hydrogen, fluorine or chlorine.

3. A compound according to claim 2, wherein $R_4$ is fluorine or chlorine.

4. A compound according to claim 2, wherein $R_5$ is fluorine or chlorine.

5. A compound according to claim 1, wherein $R_1$ is $C_1$-$C_4$-alkyl or propargyl; $R_2$ and $R_3$ are each fluorine, chlorine or bromine; $R_4$ is fluorine or chlorine; and $R_5$ is hydrogen or fluorine.

6. A compound according to claim 5, wherein $R_4$ and $R_5$ are each fluorine.

7. A compound according to claim 5, wherein $R_5$ is hydrogen.

8. A compound according to claim 6 of the formula

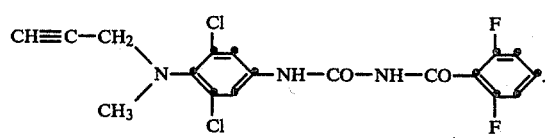

9. A compound according to claim 5 of the formula

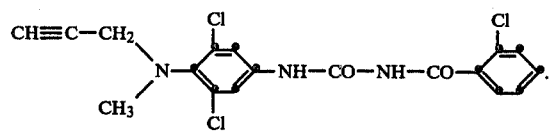

10. A compound according to claim 5 of the formula

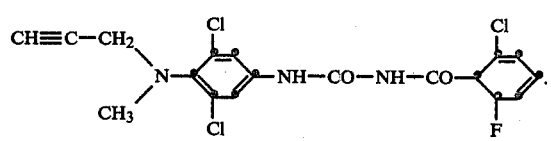

11. A compound according to claim 6 of the formula

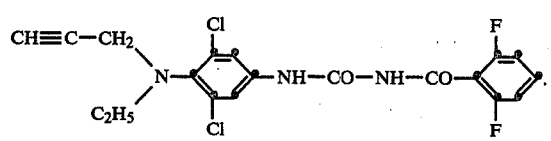

12. A compound according to claim 6 of the formula

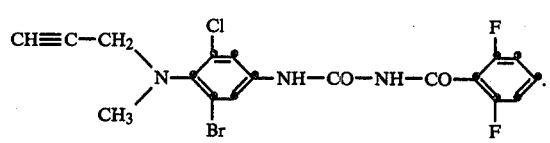

13. A compound according to claim 5 of the formula

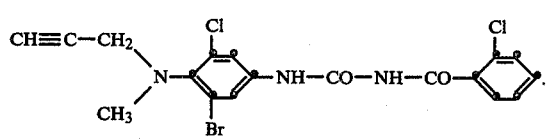

14. A compound according to claim 6 of the formula

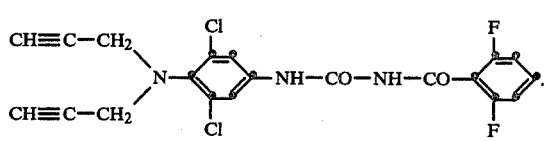

15. A pesticidal composition which contains as active ingredient a compound according to claim 1 together with suitable carriers and/or other additives.

16. A method of combating pests, which method comprises applying thereto or to the locus thereof a pesticidally effective amount of a compound according to claim 1.

* * * * *